(12) United States Patent
Martin et al.

(10) Patent No.: US 7,285,303 B2
(45) Date of Patent: Oct. 23, 2007

(54) POWDER MATERIAL FOR ELECTROSTATIC APPLICATION TO A SUBSTRATE AND ELECTROSTATIC APPLICATION OF THE POWDER MATERIAL TO A SUBSTRATE

(75) Inventors: Trevor Ian Martin, Burlington (CA); Linda Ann Reeves, Chislehurst (GB)

(73) Assignee: Phoqus Pharmaceuticals Limited, West Malling, Kent (GB)

(*) Notice: Subject to any disclaimer, the term of this patent is extended or adjusted under 35 U.S.C. 154(b) by 0 days.

(21) Appl. No.: 10/182,550

(22) PCT Filed: Feb. 1, 2001

(86) PCT No.: PCT/GB00/00425

§ 371 (c)(1),
(2), (4) Date: Dec. 17, 2002

(87) PCT Pub. No.: WO01/57144

PCT Pub. Date: Aug. 9, 2001

(65) Prior Publication Data

US 2003/0113445 A1  Jun. 19, 2003

(30) Foreign Application Priority Data

Feb. 1, 2000 (GB) .................. 0002305.1

(51) Int. Cl.
B05D 7/00 (2006.01)
B05D 1/06 (2006.01)
A61J 3/02 (2006.01)

(52) U.S. Cl. .................. 427/2.14; 427/2.21; 427/475; 427/485; 427/214

(58) Field of Classification Search ........ 427/458–486, 427/2.14–2.23, 212–222
See application file for complete search history.

(56) References Cited

U.S. PATENT DOCUMENTS

| 2,698,814 A | 1/1955 | Ransburg |
| 3,764,538 A | 10/1973 | Shelffo |
| 3,900,000 A | 8/1975 | Gallen |
| 4,029,757 A | 6/1977 | Mlodozeniec et al. |
| 4,128,445 A | 12/1978 | Sturzenegger et al. |
| 4,176,175 A | 11/1979 | Maekawa et al. |
| 4,197,289 A | 4/1980 | Sturzenegger et al. |
| 4,201,834 A | 5/1980 | Hannon et al. |

(Continued)

FOREIGN PATENT DOCUMENTS

DE  2 247 701  4/1974

(Continued)

OTHER PUBLICATIONS

Kirk-Othmer, Encyclopedia of Chemical Technology, 3 ed., vol. 19, pp. 1-2 (1982).

(Continued)

*Primary Examiner*—Fred J. Parker
(74) *Attorney, Agent, or Firm*—Nixon & Vanderhye (57) ABSTRACT

Method of electrostatically applying powder material to a substrate, wherein the substrate is a pharmaceutical substrate and the powder material is pharmaceutically acceptable. At least some of the particles of the material comprise a core and a shell surrounding the core, and the material of the core and the shell have different physical and/or chemical properties.

21 Claims, 1 Drawing Sheet

U.S. PATENT DOCUMENTS

| | | | |
|---|---|---|---|
| 4,256,805 A * | 3/1981 | Tugukuni et al. | |
| 4,322,449 A | 3/1982 | Voss et al. | |
| 4,349,531 A | 9/1982 | Mlodozeniec et al. | |
| 4,359,483 A | 11/1982 | Kaetsu et al. | |
| 4,407,444 A | 10/1983 | Knebel et al. | |
| 4,427,712 A | 1/1984 | Pan | 427/13 |
| 4,433,076 A | 2/1984 | Bauer et al. | |
| 4,454,125 A | 6/1984 | Demopoulos | |
| 4,482,387 A | 11/1984 | Wood et al. | |
| RE31,764 E | 12/1984 | Voss et al. | |
| 4,543,370 A | 9/1985 | Porter et al. | |
| 4,547,571 A | 10/1985 | Mukohyama et al. | |
| 4,548,825 A | 10/1985 | Voss et al. | |
| 4,704,295 A | 11/1987 | Porter et al. | |
| 4,786,505 A | 11/1988 | Lovgren et al. | |
| 4,800,079 A | 1/1989 | Boyer | |
| 4,810,501 A | 3/1989 | Ghebre-Sellassie et al. | |
| 4,816,264 A * | 3/1989 | Phillips et al. | 424/468 |
| 4,828,840 A | 5/1989 | Sakamoto et al. | |
| 4,925,670 A | 5/1990 | Schmidt | |
| 4,935,246 A | 6/1990 | Ahrens | |
| 4,994,273 A | 2/1991 | Zentner et al. | |
| 5,011,694 A | 4/1991 | Nuernberg et al. | |
| 5,076,706 A | 12/1991 | Shibuya et al. | |
| 5,206,030 A | 4/1993 | Wheatley et al. | |
| 5,320,796 A | 6/1994 | Harashima et al. | |
| 5,411,730 A | 5/1995 | Kiroptin et al. | |
| 5,436,026 A | 7/1995 | Berta | |
| 5,470,603 A | 11/1995 | Staniforth et al. | |
| 5,474,786 A | 12/1995 | Kotwal et al. | |
| 5,540,995 A | 7/1996 | Kitano et al. | |
| 5,615,614 A | 4/1997 | Van Pelt | 101/488 |
| 5,699,649 A | 12/1997 | Abrams et al. | |
| 5,714,007 A | 2/1998 | Pletcher et al. | |
| 5,792,513 A | 8/1998 | Koslow et al. | |
| 5,846,595 A | 12/1998 | Sun et al. | |
| 5,857,456 A | 1/1999 | Sun et al. | |
| 6,026,809 A | 2/2000 | Abrams et al. | |
| 6,074,688 A | 6/2000 | Pletcher et al. | |
| 6,117,479 A | 9/2000 | Hogan et al. | |
| 6,294,024 B1 | 9/2001 | Sun et al. | |
| 6,298,847 B1 | 10/2001 | Datta et al. | |
| 6,319,541 B1 | 11/2001 | Pletcher et al. | |
| 6,326,149 B1 | 12/2001 | Loewy et al. | |
| 6,406,738 B1 | 6/2002 | Hogan et al. | |
| 6,406,745 B1 * | 6/2002 | Talton | 427/213 |
| 6,783,768 B1 | 8/2004 | Brown et al. | |
| 2001/0018098 A1 | 8/2001 | Sun et al. | |

FOREIGN PATENT DOCUMENTS

| | | |
|---|---|---|
| DE | 3106984 | 2/1982 |
| DE | 30 49 179 A1 | 7/1982 |
| DE | 3041979 A1 | 7/1982 |
| EP | 0 011 268 A1 | 5/1980 |
| EP | 0 020 181 | 12/1980 |
| EP | 0 063 014 A2 | 10/1982 |
| EP | 0 063 014 B1 | 10/1982 |
| EP | 0 107 557 A1 | 5/1984 |
| EP | 0 063 014 B1 | 8/1985 |
| EP | 0 164 959 A2 | 12/1985 |
| EP | 0 220 670 A2 | 5/1987 |
| EP | 0 259 749 A1 | 3/1988 |
| EP | 0 277 741 A1 | 8/1988 |
| EP | 0 277 741 B1 | 8/1988 |
| EP | 0 307 642 A2 | 3/1989 |
| EP | 0 452 862 A2 | 10/1991 |
| EP | 0 459 048 | 12/1991 |
| EP | 0 459 048 B1 | 12/1991 |
| EP | 277 741 * | 9/1992 |
| EP | 0 536 791 A1 | 4/1993 |
| EP | 0 536 791 B1 | 4/1993 |
| EP | 0 543 541 A1 | 5/1993 |
| EP | 0 551 700 A1 | 5/1993 |
| EP | 0 551 700 A1 | 7/1993 |
| EP | 0 551 700 B1 | 7/1993 |
| EP | 0 567 201 A2 | 10/1993 |
| EP | 0 567 201 B1 | 10/1993 |
| EP | 0 607 009 A1 | 7/1994 |
| EP | 0 661 091 A1 | 7/1995 |
| EP | 0 661 091 B1 | 7/1995 |
| EP | 0 678 561 A3 | 10/1995 |
| EP | 0 678 564 A3 | 10/1995 |
| EP | 0 678 564 B1 | 10/1995 |
| EP | 0 551 700 B1 | 4/1997 |
| FR | D 24 084 | 11/1966 |
| GB | 1075404 | 7/1967 |
| GB | 1108837 | 4/1968 |
| GB | 1 561 100 | 2/1980 |
| GB | 2 056 885 | 3/1981 |
| GB | 2 065 691 A | 7/1981 |
| GB | 2 129 301 A | 5/1984 |
| GB | 2 179 254 A | 3/1987 |
| GB | 2 203 336 A | 10/1988 |
| GB | 2 241 889 A | 9/1991 |
| GB | 2 253 164 A | 9/1992 |
| GB | 2 253 164 B | 10/1994 |
| WO | 91/16041 | 10/1991 |
| WO | 92/11002 | 7/1992 |
| WO | 92/14451 | 9/1992 |
| WO | 94/05263 | 3/1994 |
| WO | 94/11446 | 5/1994 |
| WO | 96/02236 | 2/1996 |
| WO | 96/11707 | 4/1996 |
| WO | 96/35413 * | 11/1996 |
| WO | 96/35516 | 11/1996 |
| WO | 96/35413 * | 12/1996 |
| WO | 96/39257 | 12/1996 |
| WO | 97/04827 | 2/1997 |
| WO | 97/37775 | 10/1997 |
| WO | 97/37803 | 10/1997 |
| WO | 97/38480 | 10/1997 |
| WO | 97/47346 | 12/1997 |
| WO | 97/47347 | 12/1997 |
| WO | 99/06593 | 2/1999 |
| WO | 99/06814 | 2/1999 |
| WO | 99/13817 | 3/1999 |
| WO | 96/39256 | 12/1999 |
| WO | WO 00/69986 | 11/2000 |

OTHER PUBLICATIONS

Chemical Abstracts, vol. 120, No. 20, (1994), Grosvenor M.P. Diss. Abstr. Int., vol. 53, No. 7 (1991) Bath, p. 3492, Grosvenor M.P.
Bocchi, G.J., "Powder Coating The Complete Finishers Handbook"; *Published by The Powder Coating Institute*; pp. 1-7; (1994).
PCT/GB96/01101, International Search Report, Sep. 5, 1996, 4 pgs.
PCT/GB96/01101, International Preliminary Examination Report, Aug. 18, 1997, 11 pgs.
Examination Report under Section 18(3), Application No. GB 9723708.5 dated May 27, 1998, 4 pgs.
EP Official Action, Application No. 96 913 629 0-2114, dated Oct. 8, 1999, 2 pgs.
EP Official Action, Application No. 96 913 629 0-2114, dated Jan. 22, 2001, 3 pgs.
Gowling Lafleur Henderson LLP, Canadian Intellectual Property Office Official Action, Application No. 2,220,506, dated Feb. 17, 2005, 4 pgs.
EP Combined Search Report and Examination Report under Sections 17 and 18(3), Application No. GB 9828580.2, dated Feb. 4, 1999, 2 pgs.
EP Communication pursuant to Article 96(2) EPC, Application No. 00 117 256.8-2108, dated May 5, 2003, 3 pgs.

EP Communication pursuant to Article 96(2) EPC, Application No. 00 117 256.8-2108, dated Apr. 8, 2005, 3 pgs.

Eschborn/Tanus; Pharmazeutische Stoffliste 13. Auflage; List of Pharmaceutical Substances 13$_{th}$ Edition; *Bearbeitet und herausgegeben von Prepared and published by Pharma-Daten-Service*; pp. 230-231, (Sep. 2003).

EP Communication pursuant to Article 96(2) EPC, Application No. 97 912 341.1-2114, dated Jan. 24, 2002, 3 pgs.

EP Examination Report under Section 18(3), Application No. GB 9911055.3, dated Mar. 28, 2000, 3 pgs.

EP Combined Search Report and Examination Report under Sections 17 and 18(3), Application No. GB 0103413.1, dated Mar. 23, 2001, 2 pgs.

Gowling Lafleur Henderson LLP, Canadian Intellectual Property Office Official Action, Application No. 2,279,841, dated Dec. 13, 2004, 3 pgs.

PCT International Preliminary Examination Report, International Application No. PCT/GB97/03121, dated Feb. 12, 1999.

Kirk-Othmer, Encyclopedia of Chemical Technology, Third Edition, vol. 19; "Powder Coatings to Recycling", 4 pgs.

EP Communication pursuant to Article 96(2) EPC, Application No. 01 948 995.4-1214, dated Dec. 6, 2004, 3 pgs.

EP Communication pursuant to Article 96(2) EPC, Application No. 01 948 995.4-1214, dated Jun. 26, 2003, 3 pgs.

EP Examination Report under Section 18(3), Application No. GB 0217155.1, dated Jun. 5, 2003, 3 pgs.

PCT Notification of Transmittal of the International Preliminary Examination Report, Int'l Application No. PCT/GB01/00425, dated Jun. 6, 2002, 17 pgs.

\* cited by examiner

Fig. 1

POWDER MATERIAL FOR ELECTROSTATIC APPLICATION TO A SUBSTRATE AND ELECTROSTATIC APPLICATION OF THE POWDER MATERIAL TO A SUBSTRATE

FIELD OF THE INVENTION

This invention relates to a powder material suitable for electrostatic application to a substrate, and to a method of electrostatically applying the powder material to a substrate. In particular, but not exclusively, the invention relates to powder material and its application to the surface of solid dosage forms, for example tablets, especially pharmaceutical solid dosage forms.

A "dosage form" can be formed from any material that can be apportioned into individual units; it may be, but is not necessarily, an oral dosage form. Examples of pharmaceutical solid dosage forms include pharmaceutical tablets, pharmaceutical pessaries, pharmaceutical bougies and pharmaceutical suppositories. The term "pharmaceutical tablet" should be interpreted as covering all pharmaceutical products which are to be taken orally, including pressed tablets, pellets, capsules and spherules. The term "solid dosage form" does not, however, include products such as small pellets and granules where a large number are utilised to provide a single dosage, for example small pellets which are filled into capsule shells for administration, and granules which are compressed to form tablets or sprinkled on the food or drink; such pellets or granules are not themselves each solid dosage forms but rather, when combined together, for example in a capsule or tablet, define in combination a solid dosage form. Examples of non-pharmaceutical solid dosage forms include items of confectionery, washing detergent tablets, repellents, herbicides, pesticides and fertilisers.

The electrostatic application of powder material to a substrate is well known. The electrostatic application of powder material to a solid dosage form is also known. For example, WO 92/14451 describes a process in which the cores of pharmaceutical tablets are conveyed on an earthed conveyor belt and electrostatically charged powder is deposited on the cores to form a powder coating on the surface of the cores.

BACKGROUND TO THE INVENTION

A powder material for electrostatic application to a substrate should have certain properties. For example, the electrical properties of the powder material should be such as to make the powder material suitable for electrostatic application, and other properties of the powder material should be such that the material can be secured to the substrate once electrostatic application has taken place.

WO 96/35413 describes a powder material which is especially suitable for electrostatic application to a poorly-conducting (non-metal) substrate such as a pharmaceutical tablet. Because it may be difficult to find a single component capable of providing the material with all the desired properties, the powder material comprises a number of different components which together are capable of providing the material with all or at least as many as possible of the desired properties, the components being co-processed to form "composite particles". For example, the powder material may comprise composite particles including one component which is fusible to form a continuous film on the surface of the substrate, and another component which has desirable electrical properties.

WO 96/35413 also describes a coating material for the electrostatic coating of a substrate, wherein the coating material includes active material. The active material may be one which is physiologically active, the coating material being applied, for example, to a tablet core containing the same or a different active material or to a core containing no active material. By electrostatically applying active material to a surface of the dosage form, it has been found to be possible to apply accurately very small amounts of active material to the dosage form, leading to improved dose reproducibility.

A disadvantage of the above-mentioned powder materials, however, is that they are not readily adaptable to changes in formulation. The formulation of a powder material may be changed for a number of different reasons. For example, if the material is a coloured material, there may be a change in the colorant, or if the material is an active material, for example a physiologically active material, there may be a change in the type of active material, or in the concentration of that active material. Because all the components of the powder material are intimately mixed, any change in the components will alter the material's electrical properties and hence its performance in electrostatic application. Whenever there is a change in formulation, it may therefore be necessary, for optimum performance, to adjust the content of the component(s) that make the material suitable for electrostatic application, or perhaps even to use a different component.

There is accordingly a need for a method of electrostatically applying a powder material to a substrate, in which the powder material is more readily adaptable to changes in formulation.

SUMMARY OF THE INVENTION

The present invention provides a method of electrostatically applying a powder material to a substrate, wherein at least some of the particles of the material comprise a core and a shell surrounding the core, the core and the shell having different physical and/or chemical properties. Commonly, the majority of the particles of the material and, generally, substantially all the particles of the material comprise a core and a shell.

Generally, the shell and the core have a different composition. Advantageously, at least one component is present in the shell that is not present in the core or, especially, at least one component is present in the core that is not present in the shell, or both shell and core contain a component or components that are not found in the core or shell respectively. The shell may, if desired, comprise one or more layers.

Where the particles of the powder material of the present invention comprise a core and a shell surrounding the core, it is possible to place those components which are likely to be altered, for example colorant and active material, in the core, and to provide a more universal shell composition which is suitable for use with various core compositions, so that alterations may be made to the components that are in the core without substantially affecting the overall suitability of the powder material; thus, the shell ensures that the change in composition of the core does not affect the performance of the material in electrostatic application. Accordingly, alterations to one component of the powder material may be made with minimum alteration in the amounts of other components.

Accordingly, the present invention especially provides a method of preparing a number of different powder materials for electrostatic application to pharmaceutical substrates, the particles of each of the powder materials comprising a core and a shell surrounding the core, which method comprises, for each powder material, encapsulating the desired core material, the core material suitably comprising a binder polymer and one or more additives selected from a colorant, an opacifier, a biologically active material and a filler and optionally one or more other additives, with a shell material having different physical and/or chemical properties from the core material and suitably comprising a binder polymer and optionally one or more other additives, and wherein the same shell material is used for the different powder materials produced.

DETAILED DESCRIPTION OF THE INVENTION

Generally, the powder material includes a component which is fusible, and that component may be present in the shell or in the core or in both the shell and the core. Advantageously, the fusible component is treatable to form a continuous film coating. Examples of suitable components are as follows: polyacrylates, for example polymethacrylates; polyesters; polyurethanes; polyamides, for example nylons; polyureas; polysulphones; polyethers; polystyrene; polyvinylpyrrolidone; biodegradable polymers, for example polycaprolactones, polyanhydrides, polylactides, polyglycolides, polyhydroxybutyrates and polyhydroxy-valerates; polysaccharides, for example cellulose ethers and cellulose esters; sugar alcohols, for example lactitol, sorbitol, xylitol, galactitol and maltitol; sugars, for example sucrose, dextrose, fructose, xylose and galactose; hydrophobic waxes and oils, for example vegetable oils and hydrogenated vegetable oils (saturated and unsaturated fatty acids), e.g. hydrogenated castor oil, carnauba wax, and bees wax; hydrophilic waxes; polyalkenes and polyalkene oxides; polyethylene glycol. Clearly there may be other suitable materials, and the above are given merely as examples. One or more fusible materials may be present. Preferred fusible materials generally function as a binder for other components in the powder.

In general the powder material should contain at least 30%, usually at least 35%, advantageously at least 80%, by weight of material that is fusible, and, for example, fusible material may constitute up to 95%, e.g. up to 85%, by weight of the powder. Wax, if present, is usually present in an amount of no more than 6%, especially no more than 3%, by weight, and especially in an amount of at least 1% by weight, for example 1 to 6%, especially 1 to 3%, by weight of the powder material.

Of the materials mentioned above, polymer binders (also referred to as resins) should especially be mentioned. Examples include polyvinylpyrrolidone, hydroxypropyl cellulose, hydroxypropyl methylcellulose phthalate, hydroxypropyl methylcellulose acetate succinate, and methacrylate polymers, for example an ammonio-methacrylate copolymer, for example those sold under the name Eudragit. Xylitol or other sugar alcohol may be added to the polymer binder, for example when the polymer binder is insoluble, to promote solubility.

Often resin will be present in the core and the shell, with a wax as an optional further fusible component in the core; the presence of a wax may, for example, be useful where fusing is to take place by a contact system, for example using a heated roller, or where it is desired to provide a glossy appearance in the fused film. Sugar alcohol, if used, may be present in the core and/or the shell as appropriate. The fusible component may comprise a polymer which is cured during the treatment, for example by irradiation with energy in the gamma, ultra violet or radio frequency bands. For example, the core may comprise thermosetting material which is liquid at room temperature and which is hardened after application to the substrate.

Preferably a fusible component is fusible at a temperature of no more than 250° C., more especially no more than 150° C., at a pressure of no more than 100 lb/sq inch, more especially at atmospheric pressure.

Where both the shell and the core contain a component which is fusible, those components may be the same or different. Often the core and shell contain different fusible materials. A shell material may be chosen, for example, for its triboelectric charging properties and/or to provide mechanical strength to the particles. Other material is chosen, for example, for its good fusibility. Selection of the fusible component or components used may also be influenced by the end use. For example, it may be desirable to utilise a binder(s) that is fast dissolving, for example for washing detergent tablets. When different fusible materials are used, they are preferably compatible so that they can fuse together.

Preferably, the powder material includes a material having a charge-control function. That functionality may be incorporated into a polymer structure, as in the case of Eudragit resin mentioned above, and/or, for a faster rate of charging, may be provided by a separate charge-control additive. Material having a charge-control function may be present in the shell or in the core or in both shell and core. Examples of suitable charge-control agents are as follows: metal salicylates, for example zinc salicylate, magnesium salicylate and calcium salicylate; quaternary ammonium salts; benzalkonium chloride; benzethonium chloride; trimethyl tetradecyl ammonium bromide (cetrimide); and cyclodextrins and their adducts. One or more charge-control agents may be used. Charge-control agent may be present, for example, in an amount of up to 10% by weight, especially at least 1% by weight, for example from 1-2% by weight, based on the total weight of the powder material. The presence of charge-control agent in the core should especially be mentioned; in some cases, the presence of this material in the core only can be effective to establish a base charging level, despite encapsulation.

Optionally, or at least one component may be present on the outer surface of the shell. For example, the powder material may also include a flow aid present at the outer surface of the shell. The flow aid reduces the cohesive and/or other forces between the particles of the material to improve the flowability of the powder. The component may be present on the surface of the shell although in addition some may be embedded in the surface of the shell. Suitable flow aids (which are also known as "surface additives") are, for example, as follows: colloidal silica; metal oxides, e.g. fumed titanium dioxide, zinc oxide or alumina; metal stearates, e.g. zinc, magnesium or calcium stearate; talc; functional and non-functional waxes, and polymer beads, e.g. poly-methyl methacrylate beads, fluoropolymer beads and the like. Such materials may also enhance tribocharging. A mixture of flow aids, for example Often the powder material includes a colorant and/or an opacifier. Such components are preferably present in the core, although each may alternatively or in addition be present in the shell. Examples of suitable colorants and opacifiers are as follows: metal oxides, e.g. titanium dioxide, iron oxides; aluminium lakes, for example, indigo carmine, sunset yellow and tartrazine; approved food dyes; natural pigments. A mixture of such materials may be used if desired. Opacifier preferably constitutes no more than 50%, especially no more than 40%, more especially no more than 30%, for example no more than 10%, by weight of the powder material, and may be used, for example, in an amount of at least 5% by weight of the powder. Titanium dioxide is an especially useful opacifier, providing white colour and having good hiding power and tinctorial strength. Colorant present with opacifier may, for example, constitute no more than 10%, preferably from 1 to 5%, by weight of the powder. If there is no opacifier, the colorant may be, for example, 1 to 15%, e.g. 2-15%, especially 2-10%, by weight of the powder. To achieve optimum colour, amounts of up to 40% by weight of colorant may be needed in some cases, for example if inorganic pigments, e.g. iron oxides, are used. However, the powder material usually contains, for example, from 0 to 25% by weight in total of colorant and/or opacifier.

The powder material may also include a dispersing agent, for example a lecithin. The dispersing agent is preferably present with the colorant/opacifier (that is, preferably in the core), serving to improve the dispersion of the colorant and opacifier, more especially when titanium dioxide is used. The dispersing component is preferably a surfactant which may be anionic, cationic or non-ionic, but may be another compound which would not usually be referred to as a "surfactant" but has a similar effect. The dispersing component may be a co-solvent. The dispersing component may be one or more of, for example, sodium lauryl sulphate, docusate sodium, Tweens (sorbitan fatty acid esters), polyoxamers and cetostearyl alcohol. Preferably, the powder material includes at lest 0.5%, e.g. at least 1%, for example from 2% to 5%, by weight of dispersing component, based on the weight of the powder material. Most often it is about 10% by weight of the colorant+opacifier content.

Where the coating material is used for "immediate" release tablets, the powder coating material advantageously includes a disintegrant which may disrupt the coating.

The disintegrant may be one which swells rapidly and extensively on contact with moisture, thereby disrupting the coating. Some disintegrants may swell to become up to 40 times their original volume within seconds. Examples of suitable disintegrants include sodium starch glycolate (cross-linked) and sodium carboxymethyl cellulose (cross-linked).

Alternatively, or in addition, the disintegrant may be of a wicking-type which allows penetration of moisture through the coating to the substrate core, but which prevents moisture moving from the substrate core back through the coating, thereby causing rupture of the coating. Examples of suitable disintegrants of the wicking type include native starch and cross-linked polyvinylpyrrolidone (crosprovidone).

The disintegrant may be a gas-producing type, for example sodium carbonate, sodium hydrogen carbonate or sodium glycinate.

A disintegrant, if present, may be found in the shell and/or core, more especially in the core. There may, for example, be at least 0.5% by weight of disintegrant.

Preferably, the powder coating material contains no more than 10% by weight of disintegrant. Preferably, the powder contains no more than 5%, preferably no more than 2%, more preferably no more than 1%, most preferably about 0.5%, by weight of disintegrant.

The powder material may also include a plasticiser, if necessary, to provide appropriate. Theological properties. A plasticiser may be present in the core and/or the shell, but usually, if present, a plasticiser is included with resin used for the core to provide appropriate rheological properties, for example for preparation of the core by extrusion in a melt extruder. Examples of suitable plasticisers are ethyl citrate and polyethylene glycol having a molecular weight less than polyethylene glycol 6000.

A plasticiser may be used with a resin in an amount, for example, of up to 50% by weight of the total of that resin and plasticiser, the amount depending inter alia on the particular plasticiser used. Thus, the shell can contain an amount of up to 50% by weight of plasticiser, calculated on the weight of the shell resin and shell plasticiser, and/or the core can contain an amount of up to 50% by weight of plasticiser, calculated on the weight of the core resin and core plasticiser, although usually any plasticiser is present only in the core. Plasticiser may be present, for example, in an amount of at least 2% by weight based on the weight of the total powder material Where the powder material is to be applied to a dosage form for oral administration, the powder coating material may further include one or more taste modifiers, for example aspartame, acesulfame k, cyclamates, saccharin, sugars and sugar alcohols or flavourings, present in the core and/or the shell, but especially in the core. Preferably there is no more than 5%, more preferably no more than 1%, of flavouring based on the weight of the powder material, but larger or smaller amounts may be appropriate, depending on the particular taste modifier used.

In a preferred embodiment of the invention, the powder material includes active material, preferably present in the core, although such material may alternatively or in addition be present in the shell. The active material may comprise one or more compounds.

The powder material comprising active material may be applied, for example, to a solid dosage form containing the same or a different active material, or may be applied to a solid dosage form containing no active material.

The active material may be, for example, a biologically active material, that is a material which increases or decreases the rate of a process in a biological environment, and a biologically active material may be one which is physiologically active. Thus, active materials include those materials which are administered to the human or animal body, for example for the prevention and/or treatment of disease, as well as those administered in connection with a diagnostic or other investigation. The coating material comprising biologically active material may be applied to, for example, a substrate core containing the same or a different biologically active material, or may be applied to a core containing no active material.

The active material may comprise, for example, acid-peptic and motility-influencing agents, laxatives, anti-diarrhoeials, colo-rectal agents, pancreatic enzymes and bile acids, antiarrhythmics, antianginals, diuretics, anti-hypertensives, hypertensives, anti-coagulants, anti-thrombotics, fibrinolytics, haemostatics, hypolipidaemic agents, anti-anaemia and neutropenia agents, hypnotics, anxiolytics, anti-psychotics, anti-depressants, anti-emetics, anti-convulsants, CNS stimulants, analgesics, anti-pyretics, anti-migraine agents, non-steroidal anti-inflammatory agents, and other anti-rheumatics, anti-gout agents, muscle relaxants, neuro-muscular agents, steroids, hypoglycaemic agents, hyperglycaemic agents, antibiotics, anti-tuberculous drugs, anti-fungals, anti-parasite drugs, anti-malarials, anti-virals, immunosuppressants, immune modulators, nutritional agents, minerals, vitamins, electrolytes, anti-obesity drugs, anorectic agents, appetite suppressants, appetite stimulants, anti-allergenics, e.g. anti-histamines, bronchodilators, expectorants, anti-tussives, mucolytics, decongestants, anti-glaucoma agents, oral contraceptive agents, diagnostic agents, anti-neoplastic agents, drugs for treating drug-dependence, agents to combat auto-immune diseases, anti-cancer drugs, anticholinergic drugs, drugs for treating infertility and for other treatments of the female reproductive system and for treating male sex disorders, and/or drugs for treating incontinence.

In the case of washing powder tablets, the active material may be, for example, detergent, enzymes, bleach and/or fabric softener.

Active material for use in agriculture may be, for example, an insecticide, herbicide, fertiliser or pesticide, for example slug killer. Other active material may be, for example, insect repellent.

Where the uncoated dosage form does not contain active material, the amount of active material in the coating material applied to each dosage form will usually correspond to one dose of the active component or to a simple fraction of the single standard dose, for example ½ or ⅓ of a single standard dose of the active material. Alternatively, since there is often a need for a range of dosages of a particular active material, different amounts of active material may be applied to a standard dosage form optionally containing the minimum standard dosage, to provide a supply of dosage forms with a range of different dosages. It will be understood that the absolute quantity of active material applied to any dosage form will depend inter alia on the active component used and the number of solid dosage forms to be used together, for example, for a pharmaceutical, the number of dosage forms to be taken by the patient for each dose. The active material may be, for example, up to 50%, for example up to 30 or 40%, by weight, and, for example, at least 0.5% by weight, preferably at least 1% by weight, of the total weight of the powder material. With very active pharmaceutical material a much smaller proportion may be appropriate.

If desired, the powder material may further include a filler or diluent, present in the core and/or the shell. Suitable fillers and diluents are essentially inert and low-cost materials with generally little effect on the colour or other properties of the powder. Examples are as follows: alginic acid; bentonite; calcium carbonate; kaolin; talc; magnesium aluminium silicate; and magnesium carbonate. Filler may be used, for example, interchangeably with active material in the preparation of a range of powder materials with different active material contents. For example, a formulation used as a basis for a range of powders may be supplemented by a constant amount of further material consisting of active material, active material and filler, or filler. Thus, for example, a basic formulation which constitutes 60% of the final powder material may contain, for example, an additional 40% active material, 30% active material plus 10% filler, 20% active material plus 20% filler, or 10% active material plus 30% filler, the percentages being calculated on the final powder material in each case.

Although it is preferable for the core to contain all of the ingredients which might be altered, that may not always be possible. For example, the powder material may comprise a very high proportion of active material, for example, up to 60% active material, which would result in unacceptably large particles it the core were also to contain all the other ingredients that might be altered. In such cases, for example, the shell may therefore contain additional ingredients, for example, colorant.

The proportions in which the components of the powder material are mixed is largely dependent on the materials comprising the powder material and the nature of the substrate to be coated. The proportions will be adjusted so that the desired properties of the powder material are obtained. Examples of suitable proportions for a powder material would be:

Powder Materials Not Containing an Active Material:
  Composition 1
    83% by weight resin,
    0-3% by weight wax,
    11-14% by weight inorganic colorant,
    1-2% by weight charge-control agent,
    1% by weight flow aid (external additive).
  Composition 2
    90% by weight resin,
    2% by weight wax,
    5% by weight colorant,
    2% by weight charge-control agent,
    1% by weight flow aid (external additive).
  Composition 3
    60% by weight resin having charge-control functionality
    20% by weight xylitol
    15% by weight opacifier
    3.5% by weight colorant,
    1.5% by weight dispersant
  Composition 4
    83% by weight resin
    10% by weight opacifier
    2% by weight colorant,
    2% by weight dispersant
    2% by weight charge-control agent
    0.5% by weight disintegrant
    0.5% by weight flow aid (external additive)

Powder Material Containing an Active Material
  Composition 5
    40% by weight resin(s)
    50% by weight active material
    2% by weight wax,
    5% by weight colorant,
    2% by weight charge-control agent,
    1% by weight flow aid (external additive).
  Composition 6
    45% by weight fusible component having charge-control functionality
    40% by weight active material
    5% by weight filler
    5% by weight opacifier,
    1% by weight colorant
    1.5% by weight dispersant
    1% by weight charge-control agent
    0.5% by weight taste modifier
    1% by weight flow aid (external additive)
  Composition 7
    45% by weight fusible component having charge-control functionality
    30% by weight active material
    15% by weight filler
    5% by weight opacifier
    1% by weight colorant
    1.5% by weight dispersant,
    1% by weight charge-control agent
    0.5% by weight taste modifier
    1% by weight flow aid (external additive)

If necessary, up to 50% by weight of the resin may be replaced by suitable placticiser.

The examples are provided as a guide only and are not meant to depict the limits of the invention.

In one embodiment, advantageously, the content of material in the core is maximised, with the shell being of minimum thickness consistent with its having a protecting and pacifying function to ensure the powder material has suitable mechanical and electrostatic properties. For example, the core may comprise binder and optionally one or more further materials selected from other fusible material, colorant, opacifier, dispersant, charge-control agent, disintegrant, wax, plasticiser, taste modifier, active material and filler, and the shell may comprise binder and optionally one or more further materials selected from other fusible material, colorant, dispersant, active material and charge-control agent. 10 to 20%, e.g. 10%, of the powder may, for example, be used to make up the shell. In one embodiment this is made up predominantly of resin.

Thus, for example, in the examples given above, usually the wax, colorant/opacifier, dispersant, disintegrant, filler and taste modifier as applicable, will be present in the core, as will the majority of the resin and active material when present. The xylitol may be present in the core and/or shell according, for example, to solubility requirements. Charge-control agent may also be present in the shell and/or the core. The shell may consist, for example, of resin. For example, the shell, consisting of resin, may be 10% of the powder, with the remaining resin, constituting 73%, 80%, 40%, 73%, 30%, 35% or 35% of the powder, respectively, being present in the core.

The particle size of the powder material has an important effect on the behaviour of the material in electrostatic application. Although materials having a small particle size are recognised as having disadvantages such as being more difficult to produce and to handle by virtue of the materials' cohesiveness, such materials have special benefits for electrostatic application and the benefits may more than counter the disadvantages. For example, the high surface-to-mass ratio provided by a small particle increases the electrostatic forces on the particle in comparison to the inertial forces. Increasing the force on a particle has the benefit of increasing the force that causes it to move into contact with the substrate, whilst a reduction in the inertia reduces the force needed to accelerate a particle and reduces the likelihood of a particle arriving at the substrate bouncing back off the substrate. However, very small particle sizes may not be achievable where the coating material comprises a high proportion of a particular ingredient, for example a high proportion of active material.

Preferably, at least 50% by volume of the particles of the material have a particle size no more than 100 µm. Advantageously, at least 50% by volume of the particles of the material have a particle size in the range of 5 µm to 40 µm. More advantageously, at least 50% by volume of the particles of the material have a particle size in the range of 10 to 25 µm.

Powder having a narrow range of particle size should especially be mentioned. Particle size distribution may be quoted, for example, in terms of the Geometric Standard Deviation ("GSD") figures $d_{90}/d_{50}$ or $d_{50}/d_{10}$ where $d_{90}$ denotes the particle size at which 90% by volume of the particles are below this figure (and 10% are above), $d_{10}$ represents the particle size at which 10% by volume of the particles are below this figure (and 90% are above), and $d_{50}$ represents the mean particle size. Advantageously, the mean ($d_{50}$) is in the range of from 5 to 40 µm, for example from 10 to 25 µm. Preferably, $d_{90}/d_{50}$ is no more than 1.5, especially no more than 1.35, more especially no more than 1.32, for example in the range of from 1.2 to 1.5, especially 1.25 to 1.35, more especially 1.27 to 1.32, the particle sizes being measured, for example, by Coulter Counter. Thus, for example, the powder may have $d_{50}=10$ µm, $d_{90}=13$ µm, $d_{10}=7$ µm, so that $d_{90}/d_{50}=1.3$ and $d_{50}/d_{10}=1.4$.

For any particular electrostatic application method there will be an optimum particle size. Accordingly, even where there are changes in formulation, alterations in particle size should be avoided if possible. Particle size may be kept constant by altering the relative sizes of the shell and the core. For example, if the amount of active material in the core is increased (thereby increasing the core volume), the thickness of the shell may be decreased to compensate.

Figure 1:
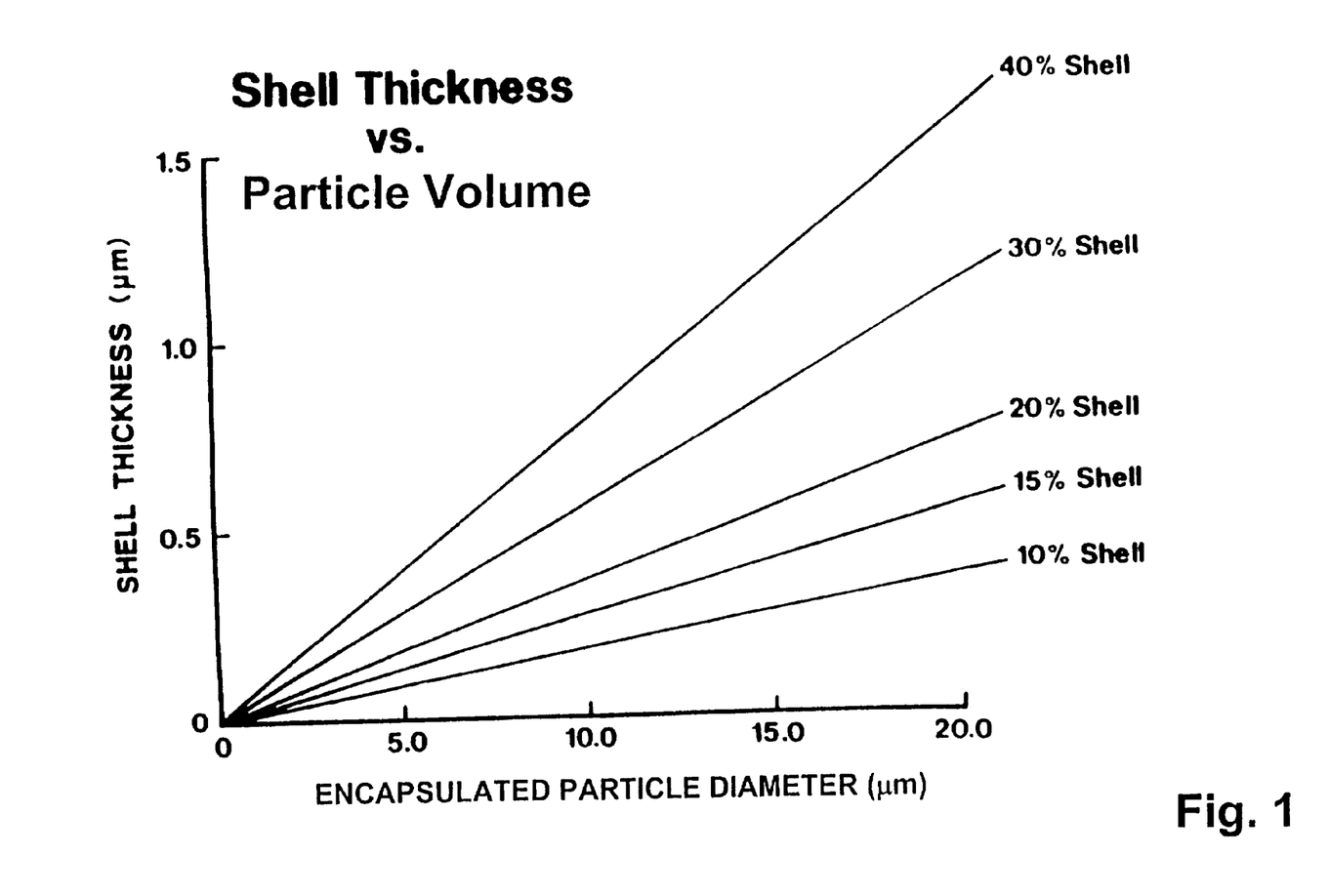

Preferably, the shell has a thickness in the range of 0.1 µm to 5 µm. Advantageously, the shell has a thickness in the range of 0.1 µm to 1.5 µm. A preferred minimum thickness is 0.2 µm; a preferred maximum is 1 µm. Thus, advantageously, the shell has a thickness in the range of 0.2 µm to 1 µm. If there are several layers comprising the shell, each shell layer will often have the above-described thicknesses, although the use of thinner layers is also possible. Shell thickness may correspond, for example, to one of the lines shown on the accompanying FIG. 1, which is a graph showing relationships between mean thickness of the shell and particle diameter for different proportions by weight of shell in relation to the whole powder. For example, for a powder of mean particle size 5 µm, with mean shell thickness 0.3 to 0.5 µm (which will provide good mechanical protection for a core of soft material), the shell may constitute approximately 30 to 45% by weight of the powder. For a powder of larger mean particle size, the same shell thickness may be obtained with a smaller proportion of shell in the total powder. Thus, for a powder with mean particle size 20 µm, the same mean shell thickness can be obtained with about 8 to 14% shell. With 10% shell, a shell thickness >0.3 µm is obtained with a mean particle size >15 µm; with 20% shell and a shell thickness >0.3 µm, the mean particle size will be >7.5 µm.

Preferably, the powder material is fusible. Advantageously, the powder material is treatable to form a continuous film coating.

It is important that the powder can be fused or treated without degradation of any active material in the powder and without degradation of the substrate. For example, many pharmaceutical substrates are sensitive to heat, particularly pharmaceutical tablet cores, which may contain organic materials. The desired temperature at which the powder material is treatable will therefore depend on the material making up the substrate. For some materials it may be possible for the treatment step to involve temperatures up to and above 250° C. Preferably, however, the powder material is fusible at a pressure of less than 100 lb/sq inch, preferably at atmospheric pressure, at a temperature of less than 200° C., and most commonly below 150° C., and often at least 80° C., for example in the range of from 120 to 140° C.

Generally, both shell and core contain fusible material, and the fusible material in both shell and core is melted on application to the substrate. If, however, the shell contains a very high melting polymer which is not melted on the substrate, the shell must be ruptured to release the core material. Rupture may be brought about by pressure and/or by expansion of the core under the action of heat. Alternatively, if the core does not contain fusible material which melts, the shell should include fusible material which will act as binder for the core material.

Fusing of the powder material may be carried out by any of a number of different fusing methods. If desired, rupture of the shell and fusing of the material may be carried out in a single step. The powder material is preferably fused by changing the temperature of the powder, for example by radiant fusing using electromagnetic radiation, for example infra red radiation or ultra-violet radiation, or conduction or induction, or by flash fusing. The amount of heat required may be reduced by applying pressure to the powder material, for example by cold pressure fusing or hot roll fusing. The powder material may also be fused by dissolution of the shell, for example by solvent vapour fusing where the powder is exposed to solvent vapour.

Preferably, the powder material has a glass transition temperature (Tg) in the range of 40° C. to 120° C. Advantageously, the material has a Tg in the range of 50° C. to 100° C. A preferred minimum Tg is 55° C., and a preferred maximum Tg is 70° C. Accordingly, more advantageously, the material has a Tg in the range of 55° C. to 70° C. Generally, the powder material should be heated to a temperature above its softening point, and then allowed to cool to a temperature below its Tg.

Advantageously, the powder material once fused is soluble in aqueous media and usually this will be at a temperature of 60° C. or below, for example at body temperature in the case of a pharmaceutical use. It may, for example, be soluble in neutral aqueous media, but it may be soluble in only a selected range of pH, for example pH 3 to pH 6 or pH 8 to pH 14 This can be especially useful for pharmaceutical use, where a drug is targeted to a particular area of the body.

Preferably, the substrate on which the powder is deposited is poorly conducting. Especially it is a non-metal substrate, and more especially is a solid dosage form, for example a tablet. Advantageously, the substrate is a pharmaceutical solid dosage form, more especially an oral pharmaceutical solid dosage form, preferably a tablet.

Preferably, the pharmaceutical solid dosage form is for human use.

Where the powder material is to be applied to a pharmaceutical solid dosage form, the powder material should of course be pharmaceutically acceptable.

The invention is, however, also of applicability to the coating of other dosage forms, which coated forms release a set quantity of active material on utilisation in their intended environment.

Any suitable method may be used to apply the powder material electrostatically to the substrate. For example, the powder may be applied by spraying electrostatically charged powder material onto the substrate, or by holding the powder material at a potential difference to the substrate sufficient to cause the powder material to be attracted thereto. Thus, the substrate may be earthed. Preferably, however, the substrate has an electrostatic charge opposite to the electrostatic charge on the powder material. The powder material may have a permanent or temporary net charge. Any suitable method may be used to charge the powder material. Advantageously, the electrostatic charge on the powder material is applied by triboelectric charging (as is common in conventional photocopying) or corona charging. The use of a charge-control agent encourages the particle to charge to a particular sign of charge and to a particular magnitude of charge. The method of the present invention is not, however, restricted to use with any particular type of electrostatic application method or apparatus. Examples of suitable methods and apparatus are described in WO 96/35516 and in our copending application PCT/US00/33962.

The present invention also provides a substrate to which powder material of the present invention has been applied by a method comprising an electrostatic application step.

The present invention further provides a powder material suitable for electrostatic application to a substrate, wherein at least some of the particles of the material comprise a core and a shell surrounding the core, the core and the shell having different physical and/or chemical properties.

The present invention also provides a powder material suitable for electrostatic application to a substrate, wherein at least some of the particles of the material comprise a core and a shell surrounding the core, the material of the core and the shell having different physical and/or chemical properties, wherein at least one component present in the core is not present in the shell and at least one component present in the shell is not present in the core and wherein the powder material is fusible at a temperature of no more than 150° C. at atmospheric pressure to form a continuous film coating, is soluble in aqueous media and includes a charge-control agent or a polymer having charge-control functionality Powder materials comprising particles having a core and a shell surrounding that core are known in various fields. For example, in the pharmaceutical field, a shell has been used to mask the taste of core ingredients, or to control release of core ingredients.

Various techniques for forming a powder material comprising particles having a core and a shell surrounding that core are known. For example, aspirin has been encapsulated by gelatin coacervation, by dispersing the aspirin with mineral oil in an aqueous gelatin solution and inducing phase separation by the addition of isopropanol and temperature reduction. Hardening was done using a formaldehyde solution.

The first step in preparing such a material is formation of the core. The core may be formed by mixing together the components of the core, and then converting the mixture into particles. The components of the core may be mixed together by, for example, melt blending or by dissolving or dispersing the components in water or some other solvent. A melt blend may then be extruded, broken into chips and ground to an appropriate particle size. A solution or dispersion may be converted into particles by, for example, wet granulation, spray drying, spray congealing, cryogenic jetting or electro-dispersion.

The second step in preparing such a material is formation of the shell by coating the core with shell material.

The shell may be formed by chemical methods, for example by interfacial or conventional in situ polymerisation, coacervation, or precipitation, by spray drying of a solution or melt, centrifugal extrusion or vacuum deposition.

In coacervation, a solution of the shell components is caused to coacervate by addition of a coacervating agent, for example gelatin, and the coacervate is then deposited on cores which are dispersed in the solution, the coacervate merging on the surface of the cores to form a coating. The coated cores are then isolated by filtration and dried. Examples of types of coacervating agent include a miscible non-solvent for the shell, a pH-adjusting solution, or an ionic solution that will precipitate the shell.

In interfacial polymerisation, for example, a solution of the shell components comprising one or more monomers for the core and a first shell monomer is emulsified by addition of an emulsifier to form emulsified droplets which are dispersed in water or a non-solvent for the core, and further shell monomer is added which is soluble in the water or the non-solvent for the core. After formation of the shell by interfacial polymerisation, free radical polymerisation of the monomer or monomers in the core can be initiated and completed. In conventional emulsion polymerisation in contrast, a monomer is polymerised around an already-formed core particle.

Physical methods may also be used for formation of the shell.

Using a Nara hybridiser, for example, smaller particles, for example of up to 0.3 micron diameter, may be applied to the surface of a larger core particle, and made to coalesce, for example by application of heat, to form a film. Monolayer shells and multilayer shells may be created in this way if desired. For example, with an oxygen-sensitive material in the core or in one layer of shell, it may be desired to provide an intermediate air-impermeable covering layer with a further top layer of high mechanical strength.

Multiple shells may also be made by other methods, for example coacervation.

In a different embodiment, the shell polymer may be added to a dispersion or suspension of core particles in a solvent for the shell polymer which is a non-solvent for the core particles. The mixture spray is subsequently dried to deposit the shell polymer on the core.

A surface additive component for the outer surface of the shell may be applied in a third step, for example by dry milling or fine powder impaction. This may be carried out as a batch process, for example in a hybridiser (a suitable one is the Nara hybridiser), or in a Henschel blender or by a continuous process, for example by a magnetically agitated impact coating process. As will be understood in the art, the process should be operated to ensure sufficient surface additive adheres to the outside of the particle, rather than becoming buried within the particle. In the case of the Nara hybridiser, for example, routine adjustment of the intensity of mixing (the rotation speed), the time of mixing and the temperature ensure the process is optimised to give the desired result.

The particle size of the powder material of the present invention will be determined predominantly by the size of the core, which is itself determined predominantly by the method selected to produce the core. Accordingly, a method should be selected which will produce cores of the desired size. When a chemical method of preparation is used involving surfactant (a suitable surfactant is polyvinyl alcohol), size will be influenced by the amount of surfactant and by the degree of agitation. Alternatively, cores of unspecified size may be prepared, and then passed through one or more sieves to separate out cores of the desired size. For example, sieves of mesh size 7 µm and 15 µm may be used to obtain a powder having particles varying in size between these limits.

A further factor affecting the particle size of the powder material is the solids loading of the shell solution. Accordingly, the solids loading of the shell should be selected to produce particles of the desired size.

The Examples which follow illustrate the invention, percentage compositions being percentages by weight, and particle size percentages being by volume.

EXAMPLES

Example 1

| Core | |
|---|---|
| Core Resin: Polyvinyl pyrrolidone | 40% |
| Colorant: Sunset Yellow | 5% |
| Opacifier: Titanium dioxide | 10% |
| Charge Control Agent: Cetrimide | 1% |
| Microcrystalline Wax | 3% |
| Active Material | 30% |
| Shell | |
| Shell resin: Eudragit E100 | 10% |
| Surface additives | |
| Hydrophilic fumed silica | 0.5% |
| Fumed titanium dioxide | 0.5% |

Preparation of the Core

The core materials are pre-mixed in a Littleford Blender or V-Mixer to ensure a uniform blend is formed, and then fed to a twin screw extruder to melt blend the material and to adequately disperse the components in the resin.

The cooled extrudate is chipped into large particles (approx. 800 microns in size) which are used as the feed for an air jet mill (micronizer). They are jetted to a mean volume particle size of 10 microns and classified to remove essentially all particles above 14 microns and all particles below 6 microns.

Preparation of Microcapsules

The core particles (18 grams) are dispersed into hexane (82 ml) using a high shear dispersion device such as a Brinkmann Homogenizer or Kady Mill. The concentration of particles in hexane is 18% solids.

In a separate vessel there is formed a 10% solution of Eudragit E100 in isopropanol. The solution of Eudragit E100 (20 ml) is added slowly and dropwise to the suspension of core particles in hexane. The Eudragit resin separates from solution and is deposited as a thin (0.2 micron) shell surrounding the individual particles.

The particles are isolated by filtration, and dried at 40 degrees C. under vacuum to remove traces of solvents (isopropanol and hexane).

Surface Treatment

The microcapsule particles, having the core-shell structure, are placed in a Waring Blender together with the surface additives and blended at high speed for a thirty second period, and then for a second sequential thirty second period to ensure that the microparticulate additives are both firmly attached and well distributed on the microcapsules.

Example 2

| Core | |
|---|---|
| Core Resin: Hydroxypropyl methylcellulose acetate succinate | 40% |
| Plasticiser: Triethyl citrate | 29.6% |
| Charge Control Agent: Benzalkonium chloride | 1% |
| Opacifier: Titanium dioxide | 10% |
| Colorant: Indigo Carmine | 2.5% |
| Colorant: Sunset Yellow | 2.5% |
| Wax: Carnauba Wax (m.p. 86° C.) | 4% |
| Shell | |
| Shell Resin: Eudragit (High Tg) | 9% |
| Charge Control Agent: Benzalkonium chloride | 1% |
| Surface additive | |
| Hydrophilic Fumed Silica | 0.4% |

Preparation of Core

The core materials are pre-mixed in a Littleford Blender or V-Mixer to ensure a uniform blend is formed, and then blended together using a heated Triple Roll Mill to melt blend the material and to adequately disperse the components in the resin.

The cooled solid blend is chipped into large particles (approx. 800 microns in size) which are used as the feed for an air jet mill (micronizer). They are jetted to a mean volume particle size of 10 microns and classified to remove essentially all particles above 14 microns and all particles below 6 microns.

Preparation of Microcapsules

The core particles (18 grams) are dispersed into hexane (82 ml) using a high shear dispersion device such as a Brinkmann Homogenizer or Kady Mill. The concentration of particles in hexane is 18% solids.

In a separate vessel there is formed a 10% solution of Eudragit (High Tg grade) in isopropanol.

The solution of Eudragit (20 ml) is added slowly and dropwise to the suspension of core particles in hexane. The Eudragit resin separates from solution and is deposited as a thin (0.2 micron) shell surrounding the individual particles.

The particles are isolated by filtration, and dried at 40 degrees C. under vacuum to remove traces of solvents (isopropanol and hexane).

Surface Treatment

The microcapsule particles, having the core-shell structure, are placed in a Waring Blender together with the surface additives and blended at high speed for a thirty second period, and then for a second sequential thirty second period to ensure that the microparticulate additives are both firmly attached and well distributed on the surface of the microcapsules.

Example 3

| Core | |
|---|---|
| Core Resin: Cellulose acetate phthalate | 20% |
| Plasticiser: Triethyl citrate | 15% |
| Opacifier: Titanium dioxide | 10% |
| Charge control Agent/Dispersant: Lecithin | 1% |
| Colorant: Red Food Dye | 4% |
| Active material | 20% |
| Inert Filler: Magnesium aluminium silicate | 15% |
| Shell | |
| Shell Resin: Polyvinyl pyrrolidone | 14.5% |
| Surface additives | |
| Alumina | 0.25% |
| Silica | 0.25% |

Preparation of Core

The core materials are melt blended using a Banbury mixer, and the crude melt blend is further melt blended by dropping the melt into the mixing zone of a heated double roll mill and subjecting the material to several cuts along the roller and re-feeding into the mixing zone.

After dispersion of the components of the core into the core resin had been achieved, the material was cooled and pulverized in a Fitz mill (hammer mill) to reduce the particle size to approximately 500 microns.

The 500 micron powder is used as the feed for an Alpine Jet mill equipped with a classifier to produce core particles of mean volume diameter (d50) of 8 micron, and a particle size distribution 1.32 (d84/d50), as measured by Coulter Counter.

Preparation of Microcapsules

A suspension of core particles in water is prepared, by dispersing 50 grams of core particles in 500 ml demineralized water.

In a separate vessel a solution of 8.5 grams of polyvinyl pyrrolidone (Kollidon K15) in 100 ml of water is prepared.

The solution of polyvinyl pyrrolidone is added to the suspension of core particles and immediately spray dried at 65° C. to form microcapsules consisting of core particles encapsulated by a thin film of polyvinyl pyrrolidone (~0.35 micron).

Surface Treatment

The microcapsule particles, having the core-shell structure, are premixed with the surface additives using the Ordered Mixing stage of a Nara Hybridizer (Nara Machinery Company). The ordered mixture is subjected to two consecutive high shear mixing cycles in the Nara Hybridizer (Hybridizer Stage) to effectively embed the additive particles onto the surface of the microcapsules.

Application to Substrate

The powder from the above Examples is coated on to pharmaceutical tablets by the method described in WO 96/35516, WO 96/35413 or PCT/US00/33962.

The invention claimed is:

1. A method of preparing a powder material and application to a pharmaceutical substrate or substrates, which method comprises
   preparing a range of pharmaceutically acceptable powder materials, the particles of each of the powder materials comprising a core and a shell surrounding the core;
   for each powder material, encapsulating a desired core material with a shell material, the core material comprising a component which can be varied selected from a binder polymer, one or more additives selected from a colorant, an opacifier, a pharmaceutically active material and a filler and optionally one or more other additives, the shell material having different physical and/or chemical properties from the core material and comprising a binder polymer and optionally one or more other additives, and wherein the same shell material is used for the range of powder materials produced; and
   electrostatically applying one or more of said powder materials produced to a pharmaceutical substrate or substrates;
   whereby a universal shell material is provided for use with various variable core compositions, permitting alterations to the components in the core without affecting electrostatic application of the powder material to a substrate.

2. A method according to claim 1, wherein different pharmaceutically active materials and/or different amounts of pharmaceutically active material are included in the range of powders prepared.

3. A method according to claim 1, wherein the core contains pharmaceutically active material.

4. A method according to claim 3, wherein active material and filler are present in the core.

5. A method according to claim 3, wherein the substrate contains a different pharmaceutically active material from the powder material.

6. A method according to claim 3, wherein the substrate contains the same pharmaceutically active material as the powder material.

7. A method according to claim 3, wherein the substrate contains no pharmaceutically active material.

8. A method according to claim 3, wherein the substrate is a pharmaceutical solid dosage form.

9. A method according to claim 1, wherein the shell comprises a binder polymer material having charge-control functionality and/or a separate charge-control agent.

10. A method according to claim 9, wherein the shell comprises a binder polymer having charge-control functionality.

11. A method according to claim 1, wherein the powder material contains one or more polymer binders selected from methacrylate polymers, polyvinylpyrrolidone, hydroxypropyl cellulose, hydroxypropyl methylcellulose phthalate and hydroxypropyl methylcellulose acetate succinate.

12. A method according to claim 1, wherein the powder material contains a methacrylate.

13. A method according to claim 12, wherein the powder material contains an ammonio-methacrylate copolymer.

14. A method according to claim 1, wherein the powder material contains polyvinylpyrrolidone.

15. A method according to claim 1, wherein the core contains a binder polymer having charge-control functionality and/or a separate charge-control agent.

16. A method according to claim 1, wherein the shell has a thickness in the range of from 0.1 µm to 5 µm.

17. A method of preparing a powder material and application to a substrate which is a solid dosage form or to a plurality of such substrates, which method comprises:
   preparing a range of powder materials, the particles of each of the powder materials comprising a core and a shell surrounding the core;
   for each powder material, encapsulating a desired core material with a shell material, the core material comprising a component which can be varied selected from a binder polymer, one or more additives selected from a colorant, an opacifier, an active material for release in the environment in which the substrate is to be used and a filler and optionally one or more other additives, the shell material having different physical and/or chemical properties from the core material and comprising a binder polymer and optionally one or more other additives, and wherein the same shell material is used for the range of powder materials produced; and
   electrostatically applying one or more of said powder materials produced to a solid dosage form or forms;
   whereby a universal shell material is provided for use with various variable core compositions, permitting alterations to the components in the core without affecting electrostatic application of the powder material to a substrate.

18. A method according to claim 17, wherein different active materials and/or different amounts of active material are included in the range of powders prepared.

19. A method according to claim 17, wherein the shell comprises a binder polymer material having charge-control functionality and/or a separate charge-control agent.

20. A method according to claim 19, wherein the shell comprises a binder polymer having charge-control functionality.

21. A method according to claim 17, wherein the powder material contains one or more polymer binders selected from methacrylate polymers, polyvinylpyrrolidone, hydroxypropyl cellulose, hydroxypropyl methylcellulose phthalate and hydroxypropyl methylcellulose acetate succinate.

* * * * *